(12) United States Patent
Cox et al.

(10) Patent No.: US 11,396,589 B2
(45) Date of Patent: Jul. 26, 2022

(54) COUPLED URACIL COMPOUND FOR VINYL CHLORIDE POLYMER RESINS

(71) Applicant: Lubrizol Advanced Materials, Inc., Cleveland, OH (US)

(72) Inventors: Adam Cox, Novelty, OH (US); Nicolas Proust, Painesville, OH (US); Jason J. Hanthorn, Eastlake, OH (US); Li Nie, Broadview Heights, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 18 days.

(21) Appl. No.: 16/654,083

(22) Filed: Oct. 16, 2019

(65) Prior Publication Data

US 2020/0048432 A1 Feb. 13, 2020

Related U.S. Application Data

(63) Continuation of application No. 15/526,158, filed as application No. PCT/US2015/061735 on Nov. 20, 2015, now abandoned.

(60) Provisional application No. 62/083,331, filed on Nov. 24, 2014.

(51) Int. Cl.
| | | |
|---|---|---|
| C08K 5/3462 | (2006.01) | |
| C08K 3/34 | (2006.01) | |
| C08K 5/098 | (2006.01) | |
| F16L 9/12 | (2006.01) | |
| C07D 239/545 | (2006.01) | |

(52) U.S. Cl.
CPC ........ *C08K 5/3462* (2013.01); *C07D 239/545* (2013.01); *C08K 3/34* (2013.01); *C08K 5/098* (2013.01); *F16L 9/12* (2013.01)

(58) Field of Classification Search
CPC . C08K 13/02; C08K 3/14; C08K 3/34; C08K 5/005
USPC ................ 138/177; 524/100; 428/34.1, 35.7
See application file for complete search history.

(56) References Cited

U.S. PATENT DOCUMENTS

| | | |
|---|---|---|
| 3,218,285 A | 11/1965 | Suling et al. |
| 3,647,451 A | 3/1972 | von Konig et al. |
| 4,178,253 A | 12/1979 | Lee et al. |
| 4,636,359 A | 1/1987 | Penninger |
| 4,656,209 A | 4/1987 | Wehner et al. |
| 5,002,865 A | 3/1991 | Kumashiro et al. |
| 5,859,100 A | 1/1999 | Friedrich et al. |
| 5,925,696 A | 7/1999 | Friedrich et al. |
| 6,084,013 A | 7/2000 | Wehner |
| 6,156,830 A | 12/2000 | Wehner et al. |
| 6,174,941 B1 | 1/2001 | Friedrich et al. |
| 6,274,654 B1 | 8/2001 | Kolb et al. |
| 6,790,885 B2 | 9/2004 | Norcini et al. |
| 6,924,330 B2 | 8/2005 | Lazzari et al. |
| 7,358,286 B2 | 4/2008 | Hopfmann et al. |
| 8,975,315 B2 | 3/2015 | Campbell |
| 2003/0109607 A1 | 6/2003 | Norcini et al. |
| 2004/0225000 A1 | 11/2004 | Heindel et al. |
| 2006/0148941 A1 | 7/2006 | Friedrich et al. |
| 2009/0131565 A1 | 5/2009 | Roth |
| 2013/0165560 A1 | 6/2013 | Belmont et al. |
| 2013/0324724 A1 | 12/2013 | Kalyan et al. |
| 2016/0017123 A1 | 1/2016 | Nie |

FOREIGN PATENT DOCUMENTS

| | | |
|---|---|---|
| DE | 3048659 | 9/1981 |
| DE | 19741778 A1 | 3/1998 |
| DE | 60106686 T2 | 2/2006 |
| EP | 0157322 | 10/1985 |
| WO | 9914204 | 3/1999 |
| WO | 200068207 | 11/2000 |
| WO | 2014/143623 A1 | 9/2014 |

OTHER PUBLICATIONS

Xu, et al., Synthesis and Application of Uracil Derivatives as Novel Thermal Stabilizers for Rigid Poly(Vinyl Chloride), Polymer Degradation and Stability 98, 2013, pp. 659-665, Elsevier, China.
Herbert Fuchs, et al., "Uber die Cyclisierung von 4-Alkylamino-5-nitrosouracilen und dieSynthese von 8-substituierten Xanthinen und Bis (theophylin-8-yl)-alkan-Derivaten", Chemische Berichte, vol. 111, No. 3, 1978, pp. 982-995.
European Patent Office, International Search Report, dated Feb. 15, 2016 for PCT/US061735.
European Patent Office, Written Opinion, dated Feb. 15, 2016 for PCT/US061735.
European Patent Office, International Preliminary Report on Patentability, dated Nov. 11, 2016 for PCT/US061735.

*Primary Examiner* — Ellen S Hock
(74) *Attorney, Agent, or Firm* — Christopher P. Demas; Teresan W. Gilbert

(57) ABSTRACT

The disclosed technology relates to a novel coupled 6-amino uracil derivative, and the use of the coupled 6-amino uracil derivative as a stabilizer in halogen containing polymer compounds. In particular, the disclosed technology relates to the use of a coupled 6-amino uracil derivative as a stabilizer in vinyl chloride compounds, such as, for example, chlorinated polyvinyl chloride (CPVC) compounds.

5 Claims, No Drawings

COUPLED URACIL COMPOUND FOR VINYL CHLORIDE POLYMER RESINS

CROSS REFERENCE TO RELATED APPLICATION

This application is a Continuation of U.S. patent application Ser. No. 15/526,158, filed on May 11, 2017 which claims priority to PCT Application Serial No. PCT/US2015/061735, filed on Nov. 20, 2015, which claims the benefit of U.S. Provisional Application No. 62/083,331 filed on Nov. 24, 2014, the entirety of which is hereby incorporated by reference.

BACKGROUND OF THE INVENTION

The disclosed technology relates to a novel coupled 6-amino uracil derivative, and the use of the coupled 6-amino uracil derivative as a stabilizer in halogen containing polymer compounds. In particular, the disclosed technology relates to the use of a coupled 6-amino uracil derivative as a stabilizer in vinyl chloride compounds, such as, for example, chlorinated polyvinyl chloride (CPVC) compounds.

Halogen containing polymers tend to degrade or deteriorate when processed. Generally, the difference between the processing temperature and the degradation temperature is very small. Therefore, there is a risk that during the processing these halogen containing polymers will degrade. When such polymers degrade, it is believed that the halide acid generated by the polymer attacks the components of the processing equipment. Also, this acid further catalyzes de-hydrohalogenation reactions, such as HCl elimination, and additional degradation of the polymer.

Stabilizers have been developed to help deter such degradation. For example, heavy metal chemical compounds such as tin are commonly used as heat stabilizers. However, heavy metal stabilizers are becoming disfavored as heat stabilizers for halogenated polymers due to environmental concerns. As a potential replacement, organic based stabilizers (OB-Stabilizers) have been developed to stabilize halogen containing polymers. First generation OB-Stabilizers have been uracil based.

Uracil is a naturally occurring pyrimidine derivative that may be represented by the formula below:

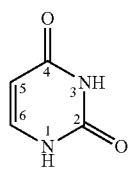

which is often N-functionalized at either or both ring nitrogens and/or at position 6, also referred to as the $C^6$ position, by an amino group.

For example, EP1044968B1 to Chemtura Vinyl Additives teaches the use of 6-amino N-functionalized uracil derivatives having the general formula I for the stabilization of chlorine-containing compounds.

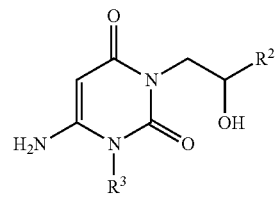

EP '968 Formula I

The EP'968 patent teaches that zeolites can be employed in combination with the uracil derivatives of formula I in amounts of about 0.1 to 20 down to about 0.1 to 5 parts by weight, based on 100 parts by weight of the chlorine-containing polymer. The EP'968 patent also teaches that alkali and alkaline earth metal chemical compounds, such as carboxylates, can be employed with the uracil derivative stabilizers. The preferred chlorine-containing polymer taught in the EP'968 patent is polyvinyl chloride (PVC). The patent does not teach or exemplify a coupled uracil, or any compound formulation including CPVC.

U.S. Pat. No. 3,436,362, to Hayer et al., issued Apr. 1, 1969 teaches a stabilized polymer composition having between 0.1 and 10 parts by weight of stabilizer per 100 parts by weight of polymer. The stabilizer is uracil and its derivatives of general formula below and the polymer can be a halogenated vinyl compound formulation, and specifically PVC.

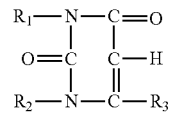

US '362 Formula

U.S. Pat. No. 4,656,209, to Wehner et al., issued Apr. 7, 1987 teaches a thermoplastic molding composition based on vinyl chloride polymers containing 0.1 to 5% by weight of an aminouracil of formula I. The patent further teaches that additional amounts of conventional PVC stabilizers may be employed, such as metal carboxylates. The patent does not teach or exemplify a coupled uracil, or any formulation containing CPVC.

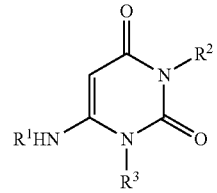

US '209 Formula I

U.S. Pat. No. 5,859,100, to Wehner et al., issued Jan. 12, 1999 teaches compositions including a rigid or semi-rigid PVC having a plasticizer content of up to 20%, and at least one aminouracil derivative chemical compound of formula 1. The patent does not teach or exemplify a coupled uracil, or any formulation containing CPVC.

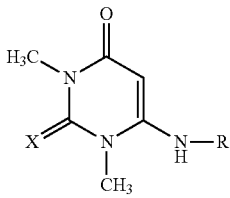

US '100 Formula 1

International application WO 2008/023249 to Chemfit Specialty Chemicals teaches a composition including an organic based stabilizer, such as uracil and its derivatives, and a smoke suppressant. Zeolites and carboxylates are disclosed as suitable smoke suppressants. The publication does not teach or exemplify a coupled uracil, or any formulation containing CPVC.

The art above does not teach or suggest the coupling of a uracil chemical compound. Further, the art is directed more toward PVC type polymers than CPVC compositions. Thus, a coupled uracil would not be readily apparent from the prior art above, nor would it be readily apparent that the use of uracil derivatives would apply to CPVC compositions.

More specifically, where heat stabilizers protect the backbone of a halogenated polymer from degrading, acid scavenger co-stabilizers prevent the loss of halogen, such as chlorine, in the form of acids, such as HCl. PVC and CPVC resins are distinctly different polymers, most particularly in the level of chlorine present in the compositions. The higher level of chlorine in CPVC resins requires different handling than PVC. For example, the higher processing temperatures required to process CPVC also require a more robust stabilizer formulation to protect the CPVC. Thus, it is not directly obvious that what will work for processing PVC formulations will work for CPVC formulations.

It would be beneficial to the industry to prepare an inexpensive and readily available alternative to current stabilizer systems for halogenated polymer compound formulations, and in particular, for CPVC compound formulations.

SUMMARY OF THE INVENTION

In one embodiment, the disclosed technology therefore solves the problem of an inexpensive readily available alternative stabilizer by providing a novel coupled uracil chemical compound. In another embodiment, the disclosed technology solves the problem of efficient stabilization in halogenated polymer compound formulations by providing a halogenated compound formulation containing the novel coupled uracil chemical compound.

Thus, one aspect of the disclosed technology provides a 6-amino coupled N-functionalized uracil derivative. In an embodiment, the 6-amino coupled N-functionalized uracil derivative can be represented by formula I:

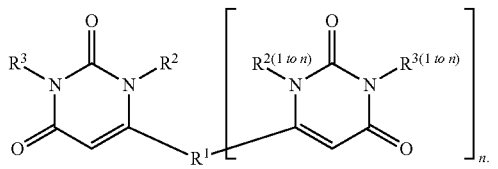

Formula I

In an embodiment of Formula I, "n" can be an integer of 1 or greater, $R^1$ can be a polyamine, polyether polyamine, or polyamine polyol, $R^2$, $R^{2(1\ to\ n)}$, $R^3$ and $R^{3(1\ to\ n)}$ can be, separately, H or a $C_1$-$C_{18}$ alkyl, $C_1$-$C_{18}$ alkyl-ester, $C_1$-$C_{18}$ alkyl-ether, or $C_1$-$C_{18}$ alcohol, and $R^1$ does not contain a nitrogen atom, $R^2$ and $R^3$ are not both H, and $R^{2(1\ to\ n)}$ and $R^{3(1\ to\ n)}$ are not both H.

In a further embodiment of Formula I, n can be 1, $R^1$ can be a $C_1$-$C_{18}$ polyamine, $C_1$-$C_{18}$ polyether polyamine, or $C_1$-$C_{18}$ polyamine polyol, and $R^2$ and $R^3$ can be, separately, $C_1$-$C_{18}$ alkyl, $C_1$-$C_{18}$ alkylester, $C_1$-$C_{18}$ alkyl-ether, or $C_1$-$C_{18}$ alcohol.

In a still further embodiment of Formula I, "n" can be 1, $R^1$ can be a $C_1$-$C_{18}$ polyamine, $C_1$-$C_{18}$ polyether polyamine, or $C_1$-$C_{18}$ polyamine polyol, $R^3$ can be H and $R^2$ can be a $C_1$-$C_{18}$ alkyl, $C_1$-$C_{18}$ alkylester, $C_1$-$C_{18}$ alkyl-ether, or $C_1$-$C_{18}$ alcohol.

In an embodiment, the 66-amino coupled N-functionalized uracil derivative can be represented by formula VII:

Formula VII

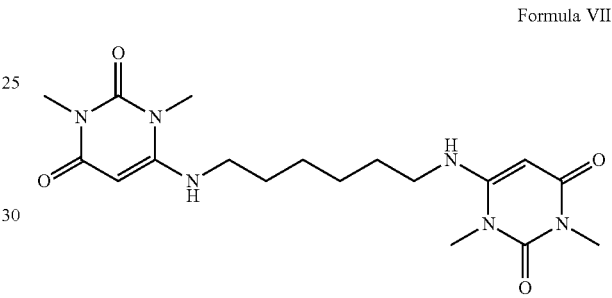

Another aspect of the disclosed technology includes a rigid halogenated polymer compound formulation, such as, for example, a CPVC compound formulation comprising (a) a halogenated polymer resin, and (b) a stabilizer including a 6-amino coupled N-functionalized uracil derivative.

In an embodiment, the rigid halogenated polymer compound can additionally contain (c) at least one of zeolite, a $C_6$ to $C_{12}$ metal carboxylate, or a combination thereof.

Another aspect of the disclosed technology includes an extruded pipe extruded from the rigid halogenated polymer compound.

In a similar aspect, there is provided fitting for joining pipe molded or extruded from the rigid halogenated polymer compound.

In a further aspect, there is provided a method of stabilizing a rigid halogenated polymer compound, such as, for example, a CPVC compound, by employing in the rigid halogenated polymer compound the 6-amino coupled uracil derivative.

DETAILED DESCRIPTION OF THE INVENTION

Various preferred features and embodiments will be described below by way of non-limiting illustration.

As used herein, the term "compound" can refer to a chemical compound, that is, a chemical substance consisting of two or more different chemical elements, or a polymer compound, that is, a blend of polymer resins and additives. Thus, the term "compound" when used in reference to, for example, a "coupled uracil chemical compound" is different than the term "compound" when used in reference to, for example, a "halogenated polymer compound formulation."

It is expected that those of ordinary skill in the art can readily discern between chemical compounds and polymer compounds. Thus, the "coupled uracil chemical compound," may be referred to alternatively as the "coupled uracil compound," or more simply as the "coupled uracil." Likewise, the "halogenated polymer compound formulation" and the like (e.g., the "CPVC compound formulation") may be referred to herein more simply as the "halogenated polymer compound" and the like (e.g., the "CPVC compound").

The present technology provides, among other things, a rigid halogenated polymer compound containing 1) a halogenated polymer resin, and 2) a stabilizer comprising, consisting essentially of, or consisting of a novel 6-amino coupled uracil derivative. As used herein, "6-amino coupled uracil derivative" refers to a uracil derivative in which carbon at the $C^6$ position is functionalized with an amino group, and the amino group is coupled, or linked, to an amino group of a neighboring 6-amino uracil derivative via a coupling, or linking group. The linking/coupling can occur via a $C_1$-$C_{18}$ alkyl, $C_1$-$C_{18}$ alkyl-ester, or $C_1$-$C_{18}$ alcohol group to form a di-, tri-, or quad-6-amino coupled uracil derivative. By "a stabilizer consisting essentially of" it is meant that the stabilizer may include some small amount of other stabilizer in amounts insignificant to the stabilization of the product, generally in the range of less than 1 phr, or less than 0.75 phr or less than 0.5 phr, or even less than 0.25 phr.

Halogenated Polymer Resin

An aspect of the technology is a rigid halogenated polymer compound, such as, for example, a polyvinyl chloride (PVC) or chlorinated polyvinyl chloride (CPVC) compound. The halogenated compound can comprise (a) a halogenated resin, such as a PVC or CPVC resin.

In a preferred embodiment, the halogenated resin is a rigid CPVC resin. Rigid CPVC in this specification can be defined according to ASTM D883. More specifically, a rigid polymer as used herein means a polymer having a either a flexural or tensile modulus of elasticity of 700 MPa (100,000 psi) or more measured at a temperature of 23° C. in an atmosphere of 50% relative humidity when tested in accordance with Test Methods ASTM D747, D790, D638, or D882.

CPVC resin, also referred to simply as CPVC, in general is comprised of a straight carbon chain backbone having hydrogen and chlorine covalently bonded and branching from individual carbon atoms along the backbone. Each carbon atom may contain from 0 to 2 chlorine atoms, as shown, for example, in formula A. Without being bound by theory, it is believed that the extent to which the carbon atoms are chlorinated can affect the properties of the CPVC, as well as any compound containing the CPVC or pipe extruded therefrom. For a typical pipe or fitting resin, CPVC according to the present invention can contain less than about 11.0 mole %, or from about 1.0 to about 10.0 mole %, or from about 3.0 to about 9.0 mole % of $CCl_2$. In general, lower amounts of $CCl_2$ are desirable for a CPVC resin. In another embodiment, CPVC according to the invention can contain from about 52.0 to about 66 mole %, or from about 54.0 to about 60.0 mole % CHCl.

Formula A

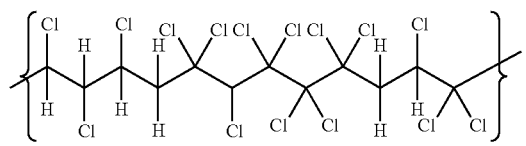

It is further contemplated in the present invention that the CPVC resin can contain some unsaturation (i.e. double bonds) along the backbone. CPVC according to one aspect of the invention can contain from about 0.0 to about 4.0 mole %, or from about 1.0 to about 3.0 mole %. For example, for every 100 carbon bonds in the CPVC backbone, from average of about 0.0 or 1.0 to an average of about 4.0 of the bonds can be unsaturated.

In contrast to CPVC, PVC contains only about 50% $CH_2$ and about 50% CHCl moieties, with no $CCl_2$ moieties and very near 0% unsaturation. As such, PVC is a much more stable polymer intrinsically than CPVC.

CPVC can be prepared by chlorinating poly(vinyl chloride) (PVC) polymer. There are considerations pertaining to the precursor PVC from which are derived the post polymerization chlorination product (CPVC) employed in this invention. The molecular weight of PVC as indicated by inherent viscosity (I.V.) measurement per ASTM D1243 should generally range from about 0.4 to about 1.4 at the extremes. Desirably, the I.V. of precursor PVC employed falls within a range of from about 0.6 to about 1.4 for pipe and fittings, generally pipe is about 0.90 to about 1.05 and generally pipe fittings are about 0.6 to about 0.8. The preferred polymerization method for preparing said PVC is the aqueous suspension method. This is the predominant method used in the art. A detailed description of the suspension process is beyond the scope of the invention and therefore will not be disclosed. The suspension process for polymerization of PVC is described in *The Encyclopedia of PVC*, Marcel Decker, Inc. (1976).

CPVC suitable for use in the instant invention may be derived from a PVC copolymer having about 5 parts or less of a co-monomer. Where the precursor PVC contains less than about 5 parts total of one or more co-monomers per 100 parts of vinyl chloride, the chlorinated version of this polymer will also be referred to herein as CPVC.

Co-monomers can include esters of acrylic acid wherein the ester portion has from 1 to 12 carbon atoms, for example, methyl acrylate, ethyl acrylate, butyl acrylate, octyl acrylate, cyano-ethyl acrylate, and the like; vinyl acetate; esters of methacrylic acid wherein the ester portion has from 1 to 12 carbon atoms, such as methyl methacrylate (MMA), ethyl methacrylate, butyl methacrylate, and the like; acrylonitrile, and methacrylonitrile; styrene derivatives having a total of from 8 to 15 carbon atoms such as alpha-methylstyrene, vinyl toluene, chlorostyrene; vinyl naphthalene; diolefins having a total of from 4 to 8 carbon atoms such as isoprene, and including halogenated olefins such as chlorobutadiene, monoolefins such as ethylene and propylene and having from 2 to 10 carbon atoms, desirably 2 to 4 carbon atoms and preferably 4 carbon atoms, with isobutylene being highly preferred. If co-monomers are used, preferred are MMA, co-polymerizable imides such as N-cyclohexyl maleimide and co-monomers known to co-polymerize with vinyl chloride monomer and yield a copolymer having a Tg equal to or higher than homo-PVC. The preferred CPVC is derived from a PVC homopolymer. It is also contemplated that a small portion of the solvent in which the PVC is polymerized can copolymerize therewith. For example, vinyl chloride can advantageously be prepared in the presence of a chain modifying co-reactant solvents such as, for example, THF, an ethylenically unsaturated alkylene such as an alpha olefin or a reactive mercaptan such as 2-mercapto ethanol, and small portions thereof may be present as comonomer in the resultant PVC.

CPVC resin is known to the art and to the literature and is commercially available. CPVC suitable for the CPVC compound disclosed herein can be made according to any commercial chlorination process or the like such as by a solution process, a fluidized bed process, a preferred water slurry process, a thermal process, or a liquid chlorine process. Reference is hereby made for example, to U.S. Pat. Nos. 2,996,049 and 3,100,762, with regard to suitable types of CPVC within the range of chlorine content which can be utilized, as well as to methods of preparation and the like.

In theory, CPVC employed herein may contain generally small amounts of non-chlorinated repeat units of vinyl chloride (VC) monomer. The amount of residual VC monomer repeat units can be from about 45.0 to about 62 wt %.

CPVC resin preferred in this specification includes CPVC having a specified weight percent (wt %) of chlorine from about 57.0 to about 70.0 wt %, more preferably, from about 60.0 to about 69.0 wt %, and even more preferably from about 63.0 to about 68.0 wt %, and most preferably between about 64.0 or 65.0 and 67.0 wt %. The wt % chlorine is based on the weight of the CPVC resin.

The CPVC resin can be included in a CPVC compound. A compound refers to a composition containing one or more resins and at least one further additives. Examples of suitable CPVC resins which can be used include the following TempRite™ CPVC resins: 674×571, 674×663 and 677×670, for example. TempRite™ is a registered trademark of Lubrizol Advanced Materials and the above enumerated resins are all commercially available from Lubrizol Advanced Materials in Cleveland, Ohio.

Stabilizer

Another aspect of the disclosed technology includes a stabilizer, wherein the stabilizer can include a 6-amino coupled uracil derivative.

More particularly, the technology includes a 6-amino coupled N-functionalized uracil derivative. The addition of the "N-functionalized" terminology means the ring N atoms in the uracil compound can be functionalized. Each uracil derivative in the coupled compound will be N-functionalized on at least one ring nitrogen with at least one of an alkyl, alkyl-ester, alkyl-ether, or alcohol. In an embodiment, the uracil derivatives can be N-functionalized on both ring nitrogen groups, individually, with at least one of an alkyl, alkyl-ester, alkyl-ether, or alcohol.

In an embodiment, the 6-amino coupled N-functionalized uracil derivative can be represented by formula I:

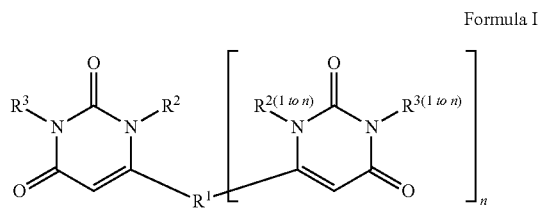

Formula I where
n can be an integer of 1 or greater, such as, for example, 1 to 5, or 1 to 4, or 1, 2 or 3;

$R^1$ can be referred to as a linking or coupling group and can be a polyamine, polyether polyamine, or polyamine polyol; and in some embodiments, $R^1$ can contain from 1 to 180 carbon atoms, or from 1 to 150 or 1 to 100 carbon atoms, and in other embodiments, from 1 to 70 or 80 carbon atoms, but generally from 1 to 18 carbon atoms, or 1 to 16, or 1 to 12 or 14, and often from 1 to 5 or 1 to 10; all with the proviso that $R^1$ does not contain a nitrogen atom; and $R^2$, $R^{2(1\ to\ n)}$, $R^{3(1\ to\ n)}$ and $R^3$ can be referred to, separately, as the N-functional groups, and can be, separately, H or a $C_1$-$C_{18}$ alkyl, $C_1$-$C_{18}$ alkyl-ester, $C_1$-$C_{18}$ alkyl-ether, or $C_1$-$C_{18}$ alcohol, that is, an alkyl, alkyl-ester, alkyl-ether, or alcohol containing from 1 to 18 carbon atoms, or from 1 to 16 or 1 to 12 carbon atoms, and in an embodiment, from 1 to 8 or 10 carbon atoms; all with the proviso that $R^2$ and $R^3$ are not both H and $R^{2(1\ to\ n)}$ and $R^{3(1\ to\ n)}$ are not both H, where $R^{2(1\ to\ n)}$ and $R^{3(1\ to\ n)}$ refer to the N-functional groups on each successive coupled derivative from n=1 to n=n.

In some embodiments, $R^2$, $R^{2(1\ to\ n)}$, $R^{3(1\ to\ n)}$ and $R^3$ can be the same and in some embodiments $R^2$, $R^{2(1\ to\ n)}$, $R^{3(1\ to\ n)}$ and $R^3$ can be different. In some embodiments, each successive $R^{2(1\ to\ n)}$ and $R^{3(1\ to\ n)}$ can be the same, or each successive $R^{2(1\ to\ n)}$ and $R^{3(1\ to\ n)}$ can be different. In general, the N-functional groups and linking groups can be customized as desired for the end purpose.

The 6-amino coupled N-functionalized uracil derivative can be prepared, in one embodiment, by reacting a molar excess of 6-halogenated N-functionalized uracil derivative with a polyamine linking group, such as, for example, a molar excess of a 6-chloro-1,3-dimethyluracil derivative reacted with a diamine or triamine.

For example, in some embodiments of formula I, $R^1$ can be a polyamine, such as, for example, a $C_1$-$C_{18}$ polyamine. The polyamines can be straight chain or branched, aliphatic or aromatic. In such an embodiment the 6-amino coupled N-functionalized uracil derivative can be prepared by reacting a molar excess of 6-chloro N-functionalized uracil derivative with the $C_1$-$C_{18}$ polyamine. The resultant 6-amino coupled N-functionalized uracil derivative can be represented, for example, by formula II:

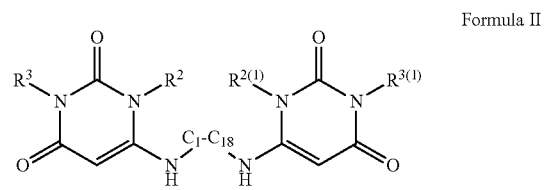

Formula II

A representative polyamine linking group can include, but not be limited to, for example, 1,6-hexanediamine.

In another example embodiment, 1$R^1$ can be a polyether polyamine, such as, for example, a $C_1$-$C_{18}$ polyether polyamine. In such an embodiment the 6-amino coupled N-functionalized uracil derivative can be prepared by reacting a molar excess of 6-chloro N-functionalized uracil derivative with the $C_1$-$C_{18}$ polyether polyamine. Commercially available polyether polyamines include, for example, the Jeffamines™ available from Huntsman. Example Jeffamines™ suitable for use can include any of those from the Jeffamine™ D series, represented by:

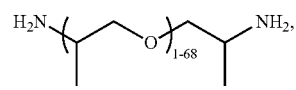

in which case the resultant 6-amino coupled N-functionalized uracil derivative can be represented, for example, by formula IV(a):

Formula IV(a)

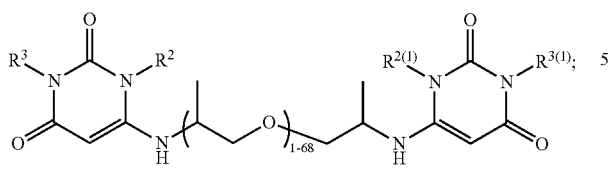

as well as the ED series, represented by:

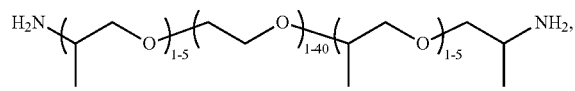

in which case the resultant 6-amino coupled N-functionalized uracil derivative can be represented, for example, by formula IV(b):

Formula IV(b)

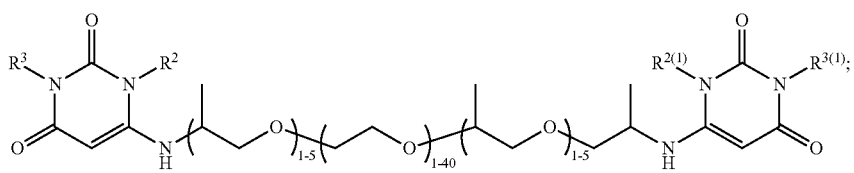

and also the EDR series, represented by:

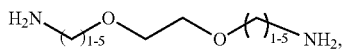

in which case the resultant 6-amino coupled N-functionalized uracil derivative can be represented, for example, by formula IV(c):

Formula IV(c)

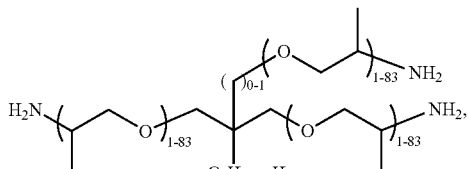

or even the T triamine series, represented by:

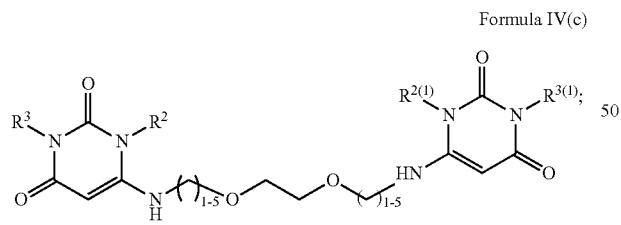

in which case the resultant 6-amino coupled N-functionalized uracil derivative can be represented, for example, by formula IV(d):

Formula IV(d)

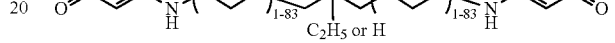

In some embodiments of formula I, $R^1$ can be a polyamine polyol. One example polyamine polyol can be, for example, as shown below:

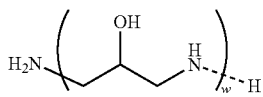

where w is an integer of from 1 to 10.

In a particular embodiment, the polyamine polyol can be derived from epichlorohydrin or derivatives thereof. In particular embodiments, epichlorohydrin can be reacted with an excess of amount of a nitrogen containing compound, such as ammonia, an amine, a polyamine, or mixtures thereof, resulting in an alcohol coupled amine, for example, according to reaction I below:

Reaction I

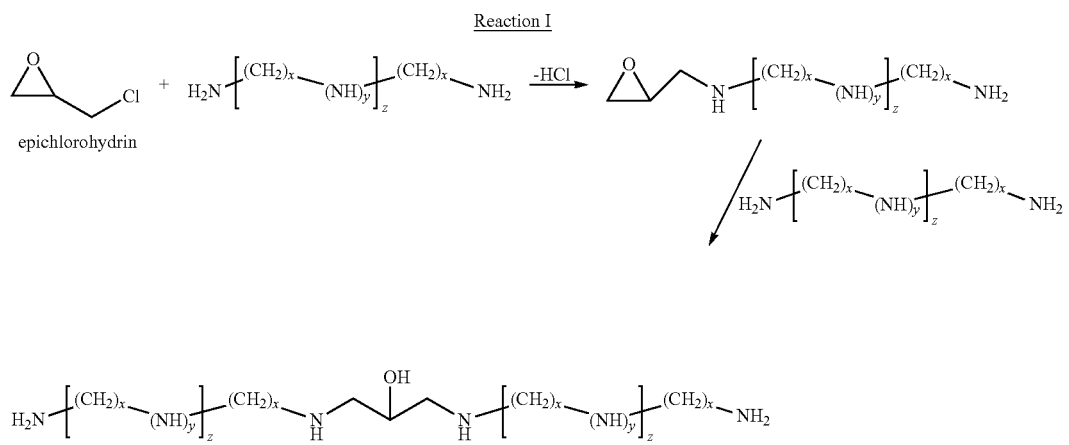

where x, y, and z are integers of from 1 to 10. The creation of a polyamine polyol can also be achieved in stages as shown, for example, in reaction II below:

Reaction II

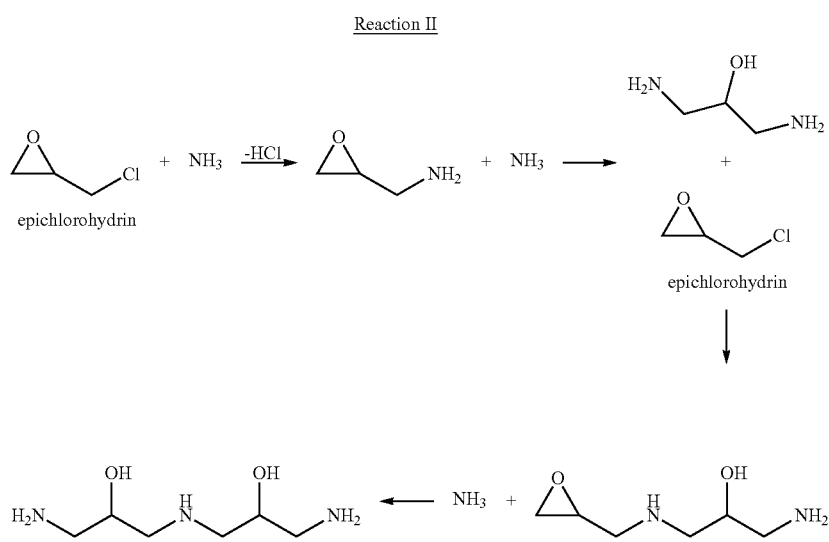

In one embodiment, the 6-amino coupled N-functionalized uracil derivative could be represented, for example, by formula V:

Formula V

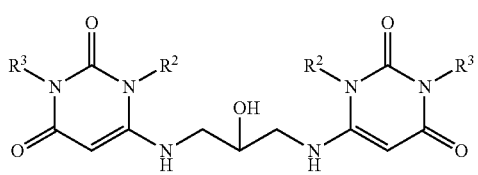

In a particular embodiment of formula I, n can be 1; $R^1$ can be a $C_1$-$C_{18}$ polyamine, $C_1$-$C_{18}$ polyether polyamine, or $C_1$-$C_{18}$ polyamine polyol; and $R^2$ and $R^3$ can be, separately, $C_1$-$C_{18}$ alkyl, $C_1$-$C_{18}$ alkylester, $C_1$-$C_{18}$ alkyl-ether, or $C_1$-$C_{18}$ alcohols. For example, in an embodiment, the 6-amino coupled N-functionalized uracil derivative can be a 6-amino coupled 1,3-methyl uracil derivative, in which the coupling group can be an $R^1$ group, that is, the 6-amino coupled N-functionalized uracil derivative can be 6,6'-($R^1$-1,[1 to 18]-diylbis(azanediyl))bis(1,3-methylpyrimidine-2,4 (1H,3H)-dione), which may, in an embodiment, be represented by formula VI:

Formula VI

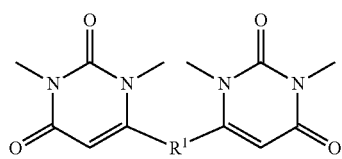

wherein $R^1$ is the same as defined above, or, in a particular embodiment, $R^1$ can be, for example, a $C_{10}$, or $C_8$ diamine or monoether diamine, or $R^1$ can be a $C_6$ alkyl, for example, and the 6-amino coupled N-functionalized uracil derivative can be represented by formula VII:

Formula VII

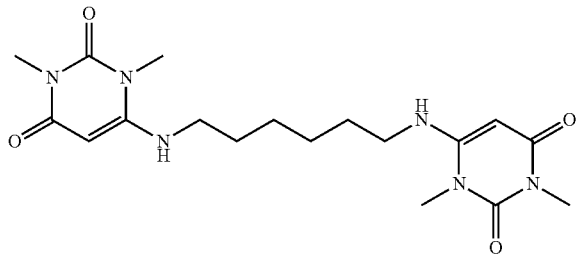

In a further embodiment of Formula I, n can be 1; $R^1$ can be a $C_1$-$C_{18}$ polyamine, $C_1$-$C_{18}$ polyether polyamine, or $C_1$-$C_{18}$ polyamine polyol; $R^2$ can be H; and $R^3$ can be a $C_1$-$C_{18}$ alkyl, $C_1$-$C_{18}$ alkylester, or $C_1$-$C_{18}$ alcohol. For example, the 6-amino coupled N-functionalized uracil derivative can be a 6-amino coupled 3-methyl uracil derivative, in which the coupling group can be an $R^1$ group, that is, the 6-amino coupled N-functionalized uracil derivative can be 6,6'-($R^1$-1,[1 to 18]-diylbis(azanediyl))bis(3-methylpyrimidine-2,4(1H,3H)-dione), which may be represented by formula VIII:

Formula VIII

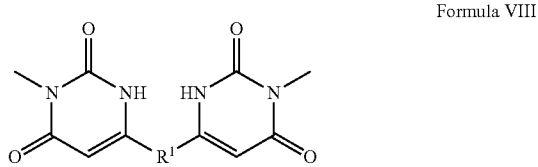

In a still further embodiment of Formula I, n can be 1; $R^1$ can be a $C_1$-$C_{18}$ polyamine, $C_1$-$C_{18}$ polyether polyamine, or $C_1$-$C_{18}$ polyamine polyol; $R^3$ can be H; and $R^2$ can be a $C_1$-$C_{18}$ alkyl, $C_1$-$C_{18}$ alkylester, or $C_1$-$C_{18}$ alcohol. In another embodiment, the 6-amino coupled N-functionalized uracil derivative can be a 6-amino coupled 1-methyl uracil derivative, in which the coupling group can be a $R^1$ group, that is, the 6-amino coupled N-functionalized uracil derivative can be 6,6'-($R^1$-1,[1 to 18]-diylbis(azanediyl))bis(1-methylpyrimidine-2,4(1H,3H)-dione), which may be represented by formula IX:

Formula IX

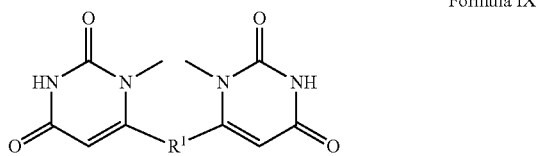

In general, the 6-amino coupled uracil derivative can be included in a halogenated polymer compound at levels required to meet physical properties, such as color. For example, the 6-amino coupled uracil derivative can be present in an amount of from about 0.05 or 0.1 to about 2.0 parts by weight per 100 parts by weight of said the halogenated polymer resin, e.g., CPVC resin. The abbreviation "phr" is used in this specification to express the amount of an additive component by weight based on 100 parts by weight of the polymer resin. In some embodiment, the 6-amino coupled uracil derivative can be present from about 0.15 to about 1.75 phr, or from about 0.2 to about 1.5 phr, or even from about 0.25 or 0.5 to about 1.25 phr.

In an embodiment, the stabilizer in the halogenated polymer compound can contain other stabilizers in addition to the 6-amino coupled uracil derivative. Examples of other stabilizers include other organic based stabilizers, zeolite, or $C_6$ to $C_{12}$ metal carboxylates.

In simplest terms, organic based stabilizers (OB-Stabilizers) are non-metal containing stabilizers based on organic chemistry. While the OB-Stabilizers suitable for the stabilizer system herein are not particularly limited, the most prevalent OB-Stabilizer compounds today include uracil and its derivatives. A common derivative of uracil suitable as an OB-Stabilizer for the composition herein is 6-amino-1,3-dimethyluracil. Other commercially available OB-Stabilizers suitable for the present composition include, for example, the Mark™ OBS™ line of stabilizers available from Galata™.

The OB-Stabilizers can be present on top of the 6-amino coupled uracil derivative in an amount to achieve the same range of from about 0.05 or 0.1 to about 2.0 phr, and in some embodiments, from about 0.15 to about 1.75 phr, or from about 0.2 to about 1.5 phr, or even from about 0.25 or 0.5 to about 1.25 phr.

Zeolites comprise basically a three dimensional framework of $SiO_4$ and $AlO_4$ tetrahedra. The tetrahedra are cross-linked through the sharing of oxygen atoms so that the ratio of oxygen atoms to the total of the aluminum and silicon atoms is equal to 2. This relationship is expressed as O/(Al+Si)=2. The electrovalence of the tetrahedra containing aluminum and silicon is balanced in the crystal by the inclusion of a cation. For example, the cation can be an alkali or alkaline earth metal ion. The cation can be exchanged for another depending upon the final usage of the aluminosilicate zeolite. The spaces between the tetrahedra of the aluminosilicate zeolite are usually occupied by water. Zeolites can be either natural or synthetic.

The basic formula for all aluminosilicate zeolites is represented as follows:

$$M_{2/n}O:[Al_2O_3]_x:[SiO_2]_y:[H_2O]_z$$

wherein M represents a metal, n represents the valence of the metal and X and Y and Z vary for each particular aluminosilicate zeolite. Essentially it is believed that any aluminosilicate zeolite can be used as a stabilizer in the instant invention, provided that the ratio of the silicon to aluminum in such aluminosilicate zeolite is less than 3.0 and that the aluminosilicate zeolite can be incorporated into the CPVC compound. Preferably, the zeolite ratio of silicon to aluminum in such aluminosilicate zeolite is less than 1.5. Most preferably, the ratio of silicon to aluminum in such aluminosilicate zeolite is about 1.

Example zeolites which can be used in the instant invention include but are not limited to zeolite A, described in U.S. Pat. No. 2,822,243; zeolite X, described in U.S. Pat. No. 2,822,244; zeolite Y, described in U.S. Pat. No. 3,130,007; zeolite L, described in Belgian Pat. No. 575,117 zeolite F, described in U.S. Pat. No. 2,996,358; zeolite B, described in U.S. Pat. No. 3,008,803; zeolite M, described in U.S. Pat. No. 2,995,423; zeolite H, described in U.S. Pat. No. 3,010,789; zeolite J, described in U.S. Pat. No. 3,011,869; zeolite P, described in U.S. Pat. No. 3,532,459, and zeolite W, described in U.S. Pat. No. 3,102,853.

The preferred zeolites can include, alone or in combination with another Group I metal, hydrated silicates of aluminum incorporating sodium, of the type $mNa_2O \cdot xAl_2O_3 \cdot ySiO_2 \cdot zH_2O$. These preferred zeolites include zeolites A, P, X, and Y.

In some embodiments, the zeolite can be present from about 0.25 to about 3.5 phr, or 0.5 to about 3.0 phr. In a preferred embodiment, the zeolite can be present from about 0.75 to about 1.5 or 2.5 phr.

The $C_6$ to $C_{12}$ metal carboxylate can be a metal salt of a saturated $C_6$, or $C_7$, or $C_8$ to $C_{11}$, or $C_{12}$ aliphatic carboxylate or dicarboxylate, an unsaturated $C_6$ to $C_{12}$ aliphatic carboxylate or di-carboxylate, a saturated $C_6$ to $C_{12}$ aliphatic carboxylate or di-carboxylate substituted with at least one OH group, or whose chain is interrupted by at least one oxygen atom (oxyacids), or a cyclic or bicyclic carboxylate or di-carboxylate containing from 6, or 7, or 8 to 11 or 12 carbon atoms. Suitable metals for the metal carboxylate can include Li, K, Mg, Ca, and Na.

Preferably the $C_6$, or $C_7$ or $C_8$ to $C_{11}$ or $C_{12}$ metal carboxylate is a sodium carboxylate, most preferably a disodium carboxylate, such as disodium sebacate, disodium dodecanedioate or disodium suberate, and combinations thereof. Other examples of $C_6$ to $C_{12}$ metal carboxylates that may be employed include disodium adipate, disodium azelate, and disodium undecanedioate.

The $C_6$ to $C_{12}$ metal carboxylate can be present from about 0.1 to about 4.0 phr. In some embodiments, the $C_6$ to $C_{12}$ metal carboxylate can be present from about 0.25 to about 3.0 phr, or 0.5 to about 2.5 phr. In a preferred embodiment, the $C_6$ to $C_{12}$ metal carboxylate can be present from about 1.0 to about 2.0 phr. The metal carboxylate can be dry blended with other ingredients of a compound or the CPVC resin can be coated with a metal carboxylate solution by a wet coating process followed by drying to obtain a metal carboxylate coated CPVC resin.

When in combination, the zeolite and $C_6$ to $C_{12}$ metal carboxylate can be present at levels that do not negatively affect the ability of the CPVC compound to meet physical property limitations and that avoid moisture foaming. With respect to moisture foaming, it has been found that including zeolite in combination with the $C_6$ to $C_{12}$ metal carboxylate at specified ratios diminishes the propensity of the zeolite to cause moisture foaming. In one embodiment the weight ratio of zeolite to the $C_6$ to $C_{12}$ metal carboxylate can be between about 6:1 to 1:6. In another embodiment, the weight ratio of zeolite to $C_6$ to $C_{12}$ metal carboxylate can be from about 5:1 to 1:5, or 4:1 to 1:4, or even 3:1 to 1:3. In some preferred embodiments the weight ratio of zeolite to $C_6$ to $C_{12}$ metal carboxylate can be from about 2:1 to 1:2, or even 1:1.

When employing a combination of zeolite and $C_6$ to $C_{12}$ metal carboxylate, the combined system can be present at levels that do not negatively affect the ability of the CPVC compound to meet physical property limitations and that avoid moisture foaming. Generally, the combined system can be present from about 0.1 to about 7.0 phr, more preferably 0.5 to about 6.0 phr, or 0.75 to about 5.0 phr. In some embodiments, the combined zeolite and $C_6$ to $C_{12}$ metal carboxylate system can be present from about 1.0 to about 4.0 phr, and more preferably 1.25 to about 3.0 phr.

In one embodiment, other co-stabilizers beside zeolite and carboxylate may also be employed in the co-stabilizer system. In an embodiment, the stabilizer system is essentially free of, or free of heavy metal stabilizers, such as tin stabilizers. By essentially free of it is meant that a minor portion may be present in amounts that do not contribute or contribute an insignificant amount to stabilization.

For most purposes, the stabilizer system including the 6-amino coupled uracil derivative, either alone or in combination with other stabilizers, including any other OB-Stabilizers, zeolites and $C_6$ to $C_{12}$ metal carboxylates can be present in the halogenated polymer compound in an amount of from about 0.1 to about 7.0 or 8.0 phr. Preferably, the stabilizer system of the combination can be present at about 0.5 to about 6, or from about 0.75 to about 5.0. In some embodiments, the stabilizer system including the 6-amino coupled 1-methyl uracil derivative and any other stabilizers can be present in amount of from about 1.0 to about 4.5, or even 1.25 to about 3.0 or 4.0 phr.

One aspect of the present technology includes a method of stabilizing a halogenated polymer compound, such as a CPVC compound by employing in the compound a stabilizer comprising, consisting essentially of, or consisting of a 6-amino coupled uracil derivative, optionally together with OB-Stabilizers, zeolites, $C_6$ to $C_{12}$ metal carboxylates, and combinations thereof.

Other Additives

The halogenated polymer compound can also contain other additives beside the aforementioned stabilizer. In addition to the halogenated polymer resin and stabilizer, other ingredients typically added to halogenated compounds can be included in the compounds of the instant invention. The amount and nature of these ingredients is dependent upon the end use of the compound. The ingredients and their amount can be tailored to meet the end-use needs by one of ordinary skill in the art.

Chlorinated polyethylene (CPE) can be added to the halogenated compounds. The CPE is a rubbery material resulting from the chlorination of polyethylene having a substantially linear structure. The polyethylene can be chlorinated by various methods including aqueous suspension, solution or gas phase methods. An example of a method for preparing CPE can be found in U.S. Pat. No. 3,563,974. Preferably, the aqueous suspension method is used to form the CPE. If used as an impact modifier, the CPE material contains from 5 to 50% by weight of chlorine. Preferably, the CPE contains from 25 to 45% by weight of chlorine. However, the CPE can comprise a mixture of chlorinated polyethylenes, provided that the overall mixture has a chlorine content in the range of about 25 to 45% by weight chlorine. CPE is commercially available from The DuPont Dow Elastomer Company. The preferred CPE materials to be used in the compound include Tyrin™ 3611P, 2000 and 3615P; all available from the DuPont Dow Elastomer Company. Tyrin is a trademark of the DuPont Dow Elastomer Company.

The halogenated compounds may also include acrylic impact modifiers. U.S. Pat. No. 3,678,133 describes the compositions conventionally referred to as acrylic impact modifiers. Generally, the acrylic impact modifier is a composite interpolymer comprising a multi-phase acrylic base material comprising a first elastomeric phase polymerized from a monomer mix comprising at least 50 wt. % alkyl methacrylate having 1-4 carbon atoms in the alkyl group and having a molecular weight of from 50,000 to 600,000. Further, the patent states that the polymerization of the rigid thermoplastic phase is preferably conducted in such a fashion that substantially all of the rigid phase material is formed on or near the surface of the elastomeric phase. Acrylic impact modifiers are polyacrylates including ($C_4$-$C_{12}$) acrylate homo or copolymers, second stage graft copolymerized with methyl methacrylate and styrene, poly(ethylhexyl acrylate-co-butylacrylate) graft copolymerized with styrene, and/or acrylonitrile and/or methyl methacrylate; polybutyl acrylate graft polymerized with acrylonitrile and styrene. Examples of suitable acrylic impact modifiers include Paraloid™ EXL-2330, KM™ 330, 334, and 365; all of which are available from Rohm and Haas. Paraloid is a trademark of the Rohm & Haas Company. Additionally Durastrength™ 200, available from Elf Atochem, and Kane Ace™ FM-10 and FM-25, available from Kaneka, are examples of commercially available acrylic impact modifiers.

Methyl butadiene styrene ("MBS") impact modifiers can also be added to the compounds of the present invention. MBS polymers are graft polymers. Generally, MBS impact modifiers are prepared by polymerizing methyl methacrylate or mixtures of methyl methacrylate with other monomers in the presence of polybutadiene or polybutadiene-styrene rubbers. Further information on MBS impact modifiers can be found in the Second Edition of the Encyclopedia of PVC, edited by Leonard I. Nass, Marcel Dekker, Inc. (N.Y. 1988, pp. 448-452). Examples of commercially available MBS impact modifiers include Paraloid KM™ 680, BTA™ 733, 751, and 753 available from Rohm & Haas, Kane Ace™ B-22 impact modifier and Kane Ace™ B-56 impact modifier available from Kaneka.

Typical of the graft copolymer impact modifiers are those generally referred to as "ABS" resins, which may generally be described as copolymers of styrene and acrylonitrile on butadiene containing rubber. ABS modifiers are usually prepared by polymerizing styrene and acrylonitrile in the presence of polybutadiene rubber. Examples of commercially available ABS impact modifiers which can be used in the instant invention include Blendex 338, Blendex 310 and Blendex 311; all available from GE Plastics. If used as the impact modifier of choice, approximately 5 parts to about 15 parts of ABS impact modifier are used. Preferably, 6 parts of the ABS impact modifier are used.

Other additives can also be added to the halogenated compounds as needed. Conventional additives known in the art as well any other additives may be used, provided that the additive does not alter the physical properties and the process stability associated with the novel compounds. Examples of additives which can be used include antioxidants, lubricants, other stabilizers, other impact modifiers, pigments, glass transition enhancing additives, processing aids, fusion aids, fillers, fibrous reinforcing agents and antistatic agents.

Exemplary lubricants are polyglycerols of di- and trioleates, polyolefins such as polyethylene, polypropylene and oxidized polyolefins such as oxidized polyethylene and high molecular weight paraffin waxes. Since several lubricants can be combined in countless variations, the total amount of lubricant can vary from application to application. Optimization of the particular lubricant composition is not within the scope of the present invention and can be determined easily by one of ordinary skill in the art. Preferably, an oxidized polyethylene is used. An example of an oxidized polyethylene is AC 629A, sold by Allied Signal. In addition to the oxidized polyethylene, preferably a paraffin wax may also be included in the compounds of the instant invention. An example of a paraffin wax is Paraffin 160F Prill from Witco.

Suitable processing aids include acrylic polymers such as methyl acrylate copolymers. Examples of process aids include Paraloid K-120ND, K-120N, K-175; all available from Rohm & Haas. A description of other types of processing aids which can be used in the compound can be found in The Plastics and Rubber Institute: International Conference on PVC Processing, Apr. 26-28 (1983), Paper No. 17.

An example of antioxidants to be used in the halogen containing compounds include Irganox 1010 (tetrakis[methylene(3,5-ditert-butyl-4-hydroxy-hydrocinnamate)]methane) sold by Ciba, if used at all.

Suitable pigments include among others titanium dioxide, and carbon black. Examples of titanium dioxide is Tiona RCL-6 and RCL-4 from Millenium Inorganics. An example of carbon black is Raven 410, available from Columbian Chemicals.

Suitable inorganic fillers include talc, clay, mica, wollastonite, silicas, and other filling agents.

The components of the unique compound can be made in any manner wherein the various components are added together and mixed under heat. For example, the appropriate amount of the CPVC resin can be added to a vessel such as Henschel mixer or a ribbon blender. The remaining ingredients of the compound can then be added thereto and mixed until the blend is homogeneous. If pellets are to be formed, the compound can be melt mixed. Melt mixing can generally occur in the temperature range of about 150 to about 250° C. Once the blend is formed, it can be processed further depending upon the desired application in any conventional manner, using extrusion or molding techniques.

If extrusion techniques are used to process the composition of the present invention, generally conventional extrusion machinery such as a multiscrew extruder or a single screw extruder are used. An extruder generally has conveying means, an intermediate screw processing means and a final die through which the material is discharged in the form of an extrudate. Generally, a multi-screw extruder is used for the extrusion of pipe. Examples of possible conventional extruders to be used to process the compounds include the following twin screw counterrotating extruder models from Cincinnati Milacron: CM 35HP, CM 55HP, CM 65HP, CM 80HP, CM 92HP. Examples of suitable conical twin screw extruders from Krauss Maffei include KMD-2/40KK and KMD-2/50KK.

CPVC compound made according to the instant technology has the following characteristics: a tensile strength in the range of about 5,000 to about 10,000 psi (as measured according to ASTM D 638-95); a Notched Izod in the range of about 1.0 to about 20 ft.lb. per inch of notch (as measured according to ASTM D 256-93A); a dynamic thermal stability of greater than 10 minutes, such as, for example, in the range of about 10 to about 60 minutes as measured by ASTM D 2538), unless otherwise specified:

1) Counter rotating batch mixing bowl is set at 190-205° C. depending on formulations, 75 grams sample is charged to the batch mixer unless otherwise specified;
2) 1 minute sample loading at 10 rpm, followed by 2 minutes gentle mixing at 1 rpm, followed by 35 rpm run until sample degrades. Stability timing starts at 35 rpm;
3) A small pinch sample is taken at 7 minutes after 35 rpm is achieved, and then every minute thereafter.

and a heat distortion temperature in the range of about 80 to about 140° C. (as measured by ASTM D 648-95). This novel compound can be formed into any article desired. Examples include but are not limited to sheet, pipe, ducts, fittings, valves, injection molded and thermoformed industrial parts, appliance housing, fabricated parts, and different containers.

In a preferred embodiment, the halogenated compound can be employed to prepare pipe.

The amount of each chemical component described is presented exclusive of any solvent or diluent oil, which may be customarily present in the commercial material, that is, on an active chemical basis, unless otherwise indicated. However, unless otherwise indicated, each chemical or composition referred to herein should be interpreted as being a commercial grade material which may contain the isomers, byproducts, derivatives, and other such materials which are normally understood to be present in the commercial grade.

It is known that some of the materials described above may interact in the final formulation, so that the components of the final formulation may be different from those that are initially added. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

EXAMPLES

Sample 1—A commercially available compound of 6-amino-1,3-dimethyluracil, available from Sigma-Aldrich

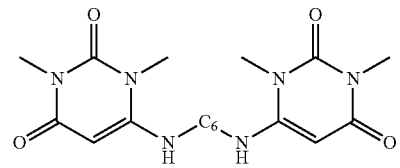

Sample 4

Examples 1 to 7

The samples were each compounded into a CPVC composition in an amount to achieve an equivalent or increased level of nitrogen compared to a 0.25 phr treat of sample 6 at control amount of Nitrogen (i.e., 1×N). The recipes for each example are shown in Table 1 below.

TABLE 1

| Ingredient | 1[3] | 2 | 3 | 4 | 5 | 6 | 7 |
|---|---|---|---|---|---|---|---|
| CPVC[1] | 100 phr | 100 phr | 100 phr | 100 phr | 100 phr | 100 phr | 100 phr |
| Sample 1 | 0.25 phr (1.26 × N) | | | | | | |
| Sample 2 | | 0.25 phr (1.22 × N) | | | | | |
| Sample 3 | | | 0.41 phr (1 × N) | 0.62 phr (1.5 × N) | 0.99 phr (2.25 × N) | | |
| Sample 4 | | | | | | 0.25 phr (1 × N) | 0.4 phr (1.5 × N) |
| Additive Package[2] | 15.515 phr | 16.015 phr | 16.015 phr | 16.015 phr | 16.015 phr | 16.015 phr | 16.015 phr |

[1]66.25Cl % 0.92 inherent viscosity.
[2]7 phr impact modifier, 4 phr coated titanium dioxide, 1.5 phr type A zeolite, 1.0 phr disodium sebacate, 2.25 phr lubricant, 0.25 phr antioxidant, 0.015 phr yellow dye.
[3]example 1 has 2.0 phr type A zeolite and no disodium sebacate.

Sample 2—Comparative dimer compound from Example 1 of U.S. Pat. No. 6,156,830, having a connection through a ring carbon
Sample 3—Comparative mono-functional alkylated Uracil derivative compound
Sample 4—Representative di-functional compound

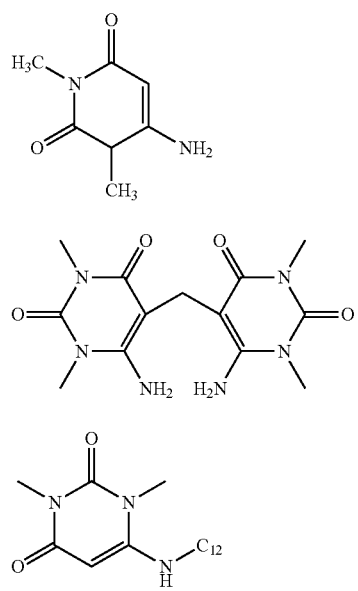

Sample 1

Sample 2

Sample 3

Color chips of each example compound were prepared using a Brabender DTS mixing unit having a counter rotating batch mixing bowl. 75 grams of each compound were loaded into the mixing bowl with the temperature of the bowl set at 190° C. Loading of the 75 gram samples was under the following conditions: (a) loading at 10 rpm for 1 minute; (b) soaking at 1 rpm for 2 minutes; (c) mixing at 35 rpm for the remainder of the test. Timing for stability started when the mixer was set to 35 rpm. A first pinch color chip sample was taken at 7 minutes, followed by another sample every 1.5 minutes until the melt was visually discolored.

The color hold stability of each pinch sample was arrived at by measuring the color change in the pinch samples compared to a color control. The 7 minute pinch sample of example 1 was used as the color chip control. The color difference was measured with a GretagMacbeth Color i7, which provides values for lightness ("L"), redgreen saturation ("a"), yellow-blue saturation ("b") and the overall color change ("ΔE"). The ΔE measurement sums up the difference in the L, a, and b values from the control. The measurements for each example are shown below in Table 2.

TABLE 2

| Time (min) | Example 1 ΔE | Example 2 ΔE | Example 3 ΔE | Example 4 ΔE | Example 5 ΔE | Example 6 ΔE | Example 7 ΔE |
|---|---|---|---|---|---|---|---|
| 7 | 0.47 | 10.75 | 3.35 | 2.27 | 1.13 | 2.05 | 1.64 |
| 8.5 | 1.01 | 12.08 | 4.8 | 2.69 | 2.53 | 2.67 | 2.09 |
| 10 | 2.1 | 13.48 | 6.08 | 4.14 | 3.14 | 3.31 | 3.03 |
| 11.5 | 2.19 | 13.66 | 7.21 | 5.05 | 4.3 | 4.59 | 3.8 |
| 13 | 3.17 | 14.62 | 8.22 | 6.08 | 5.35 | 5.85 | 4.32 |
| 14.5 | 4.63 | | 9.88 | 7.09 | 5.69 | 6.55 | 6.47 |
| 16 | 5.87 | | 11 | 8.11 | 7.39 | 7.71 | 7.2 |
| 17.5 | 7.08 | | | 8.99 | 7.86 | 8.64 | 8.48 |
| 19 | 9.44 | | | 9.72 | 9.03 | 9.53 | 9.14 |
| 20.5 | 12.34 | | | 11.1 | 10.01 | 10.9 | 10.32 |

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the essential or basic and novel characteristics of the composition or method under consideration.

While certain representative embodiments and details have been shown for the purpose of illustrating the subject invention, it will be apparent to those skilled in this art that various changes and modifications can be made therein without departing from the scope of the subject invention. In this regard, the scope of the invention is to be limited only by the following claims.

What is claimed is:

1. A rigid chlorinated vinyl chloride ("CPVC") composition comprising (a) a CPVC resin, and (b) 0.1 to 1.75 phr of a stabilizer comprising a 6-amino coupled N-functionalized uracil derivative of formula

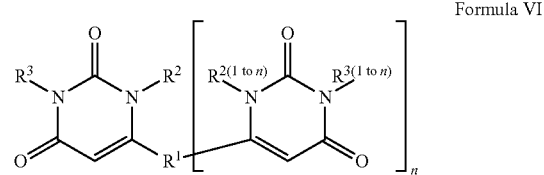

Formula VI where n is 1, $R^1$ is a $C_1$-$C_{18}$ polyamine or $C_1$-$C_{18}$ polyamine polyol, and $R^2$ and $R^3$ can be, separately, a $C_1$-$C_{18}$ alkyl, $C_1$-$C_{18}$ alkyl-ester, $C_1$-$C_{18}$ alkyl-ether, or $C_1$-$C_{18}$ alcohol.

2. The rigid CPVC composition of claim 1, wherein the stabilizer further comprises at least one of zeolite or a C6 to C12 metal carboxylate.

3. An extruded pipe comprising the rigid CPVC composition of claim 1.

4. A fitting for joining pipe sections comprising the rigid CPVC composition of claim 1.

5. A method of stabilizing a rigid CPVC composition comprising employing in the rigid CPVC composition 0.1 to 1.75 phr of a 6-amino coupled N-functionalized uracil derivative.

* * * * *